(12) United States Patent
Sabczynski et al.

(10) Patent No.: US 6,956,202 B2
(45) Date of Patent: Oct. 18, 2005

(54) METHOD AND DEVICE FOR CALIBRATING AN IMAGE PICK-UP DEVICE SENSITIVE TO MAGNETIC FIELDS AND FOR IMAGING BY MEANS OF SUCH AN IMAGE PICK-UP DEVICE

(75) Inventors: Joerg Sabczynski, Norderstedt (DE); Waldemar Zylka, Herten (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 98 days.

(21) Appl. No.: 10/294,351

(22) Filed: Nov. 13, 2002

(65) Prior Publication Data

US 2003/0095638 A1 May 22, 2003

(30) Foreign Application Priority Data

Nov. 16, 2001 (DE) .............................. 101 56 443

(51) Int. Cl.[7] ............................................ G01D 18/00
(52) U.S. Cl. .................................................. 250/252.1
(58) Field of Search ..................................... 250/252.1

(56) References Cited

U.S. PATENT DOCUMENTS

| | | | |
|---|---|---|---|
| 5,235,528 A | * | 8/1993 | Silver et al. .................... 378/7 |
| 2002/0077543 A1 | * | 6/2002 | Grzeszczuk et al. ........ 600/424 |
| 2002/0109705 A1 | * | 8/2002 | Hofstetter et al. .......... 345/647 |

FOREIGN PATENT DOCUMENTS

| | | |
|---|---|---|
| DE | 199 26 098 A1 | 12/2000 |
| EP | 0 479 618 A2 | 4/1992 |
| WO | WO 98/40847 | 9/1998 |

OTHER PUBLICATIONS

Liu, Ruijie Rachel; Super-Gloval Distortion Correction for a Rotational C-Arm X-Ray Image Intensifier; Medical Physics, American Institute of Physics; New York, US, Bd. 26, No. 9, Sep. 1999, pp. 1802-1810.

* cited by examiner

Primary Examiner—David Porta
Assistant Examiner—Shun Lee
(74) Attorney, Agent, or Firm—Douglas B. McKnight

(57) ABSTRACT

A description is given of a method and a device for the calibration of an image pick-up device which is sensitive to magnetic fields and for the imaging by means of such an image pick-up device. The image pick-up device is notably an image intensifier in X-ray systems such as, for example, systems provided with a C-arm. Calibration is performed essentially by forming and storing a look-up table whereby a plurality of magnetic field data acting on the image pick-up device is associated with calibration data required for correcting the distortions caused thereby. During imaging, the magnetic field data acting on the image pick-up device during the formation of an image is measured and the calibration data associated with this magnetic field data in the table is read out and used for the correction of the acquired image.

10 Claims, 1 Drawing Sheet

METHOD AND DEVICE FOR CALIBRATING AN IMAGE PICK-UP DEVICE SENSITIVE TO MAGNETIC FIELDS AND FOR IMAGING BY MEANS OF SUCH AN IMAGE PICK-UP DEVICE

BACKGROUND OF THE INVENTION

The invention relates to a method and a device for the calibration of an image pick-up device which is sensitive to magnetic fields, and also to a method and a device for imaging by means of such an image pick-up device, notably an image intensifier in X-ray systems, for example, X-ray systems provided with a C-arm. The invention also relates to an X-ray system provided with devices of this kind.

The images acquired by image intensifiers in X-ray systems are liable to be distorted under the influence of external magnetic fields surrounding the image intensifiers. This problem is encountered notably when the image intensifier is attached to an arm (C-arm) which is rotatable about a patient. This is because it has been found that surprisingly the magnetic field strengths may deviate strongly in different locations within an examination room. This is due to the fact that the numerous electrical and metallic components of devices customarily present in such a room and equipment as well as shields which are made partly of a ferromagnetic material have a significant effect on the magnetic field in their vicinity. In this case the external magnetic fields have a different effect on the image distortions in every position of the image intensifier. Because of the magnetic fields which strongly vary within a room, the foregoing applies even more to mobile X-ray systems which can be displaced within the room.

EP 0 479 618 discloses a method and a device enabling the correction of magnetic and geometrical distortions in an X-ray image. To this end, a calibration is performed by means of a test object provided with a grid and a calibration table is created in which the calibration data determined is associated with each pixel position in the image. The images subsequently acquired are then corrected on the basis of this table.

However, this approach has a significant drawback in that, if the external magnetic field changes after the calibration, a new calibration must be carried out before each imaging operation. In the case of a mobile X-ray system which is used in various locations it is also necessary to perform a new calibration before each imaging operation.

Therefore, it is an object of the invention to provide a method and a device which enable comparatively simple and reliable calibration of an image pick-up device which is sensitive to magnetic fields.

It is also an object of the invention to provide a method and a device which enable such a calibration to be carried out in such a manner that it need not be repeated in the case of a varying magnetic field.

It is also an object of the invention to provide a method and a device which are suitable for the compensation of the effects of magnetic fields on the imaging in particular in mobile X-ray systems.

It is a further object of the invention to provide a method and a device for imaging which are conceived notably for use in conjunction with an image pick-up device calibrated in accordance with the invention and is optionally conceived also for surgical navigation.

Finally, it is an object of the invention to provide an X-ray system which is suitable in particular for mobile applications and in which the described effects of magnetic fields can be compensated for without requiring a significant amount of additional hardware.

SUMMARY OF THE INVENTION

In conformity with claim 1 this object is achieved by means of a method for the calibration of an image pick-up device which is sensitive to magnetic fields, which method includes the following steps: determining calibration data (calibration base points) in a plurality of selected positions of the image pick-up device, which calibration data is suitable for distortion correction of an image acquired by the image pick-up device in the relevant position; determining magnetic field data acting on the image pick-up device in the respective selected positions, and associating the magnetic field data with the calibration data in a look-up table.

In this context magnetic fields are to be understood to mean the terrestrial magnetic field as well as fields which are generated or modified by devices present in the vicinity of the X-ray system.

In conformity with claim 5 the object is achieved by means of a device for carrying out the calibration method, which device is characterized in that it includes a triaxial magnetometer for determining magnetic field data acting on the image pick-up device, and an arithmetic and storage unit for forming and storing a look-up table whereby a plurality of magnetic field data determined is associated with the calibration data required for the removal of image distortions caused thereby.

The object is also achieved in conformity with claim 6 which discloses a method for imaging in particular by means of an image pick-up device calibrated in accordance with the invention, which method includes the following steps: acquiring an image of an object to be examined; determining magnetic field data then acting on the image pick-up device; comparing the magnetic field data thus determined with the magnetic field data stored in the look-up table, reading out calibration data stored in the look-up table at magnetic field data which corresponds at least essentially to the magnetic field data determined, and removing the distortions from the acquired image by means of the calibration data read out.

Finally the object is achieved in conformity with claim 9 which discloses a device for carrying out the image forming method, which device is characterized in that it includes a triaxial magnetometer for determining magnetic field data acting on the image pick-up device, an arithmetic and storage unit for comparing the magnetic field data thus determined with the magnetic field data stored in a look-up table, for reading out stored calibration data which is stored at magnetic field data which corresponds at least essentially to the magnetic field data determined, and for removing distortions from the acquired image of the object to be examined or for distorting the image of an instrument, introduced into the object to be examined, by way of the read-out and possibly interpolated calibration data, and a display unit for displaying the distortion-corrected image of the object to be examined or for displaying the distorted image of the object to be examined in which the distorted image of the instrument is reproduced.

An essential advantage of these solutions consist in that at the time of calibration the strength and the direction of the external magnetic field during the later imaging (that is, during the examination of an object) need not yet be known. Therefore, the solution in accordance with the invention is suitable in particular for three-dimensional imaging by means of mobile X-ray systems and systems comprising a C-arm which is rotated around an object to be examined, and also in general for the imaging by means of X-ray systems provided with image intensifiers. The invention can also be advantageously used for computer-aided navigation which is intended to reach given locations within an object to be examined.

Finally, it is also possible to correct distortions which arise due to a curved surface of the entrance window of the image intensifier.

The dependent claims relate to advantageous further embodiments of the invention.

In the simplest case the calibration data can be acquired by means of a phantom object as disclosed in claim 2 or be calculated by means of a physical model in conformity with claim 3.

In conformity with claim 4 the magnetic field data advantageously relates to the directions as well as the strengths of the magnetic fields.

Finally, the embodiment in conformity with claim 7 is suitable in particular for surgical navigation.

BRIEF DESCRIPTION OF THE DRAWINGS

Further details, features and advantages of the invention will become apparent from the following description of preferred embodiments, given by way of example, with reference to the drawing. Therein.

DESCRIPTION OF THE INVENTION

Figure 1:
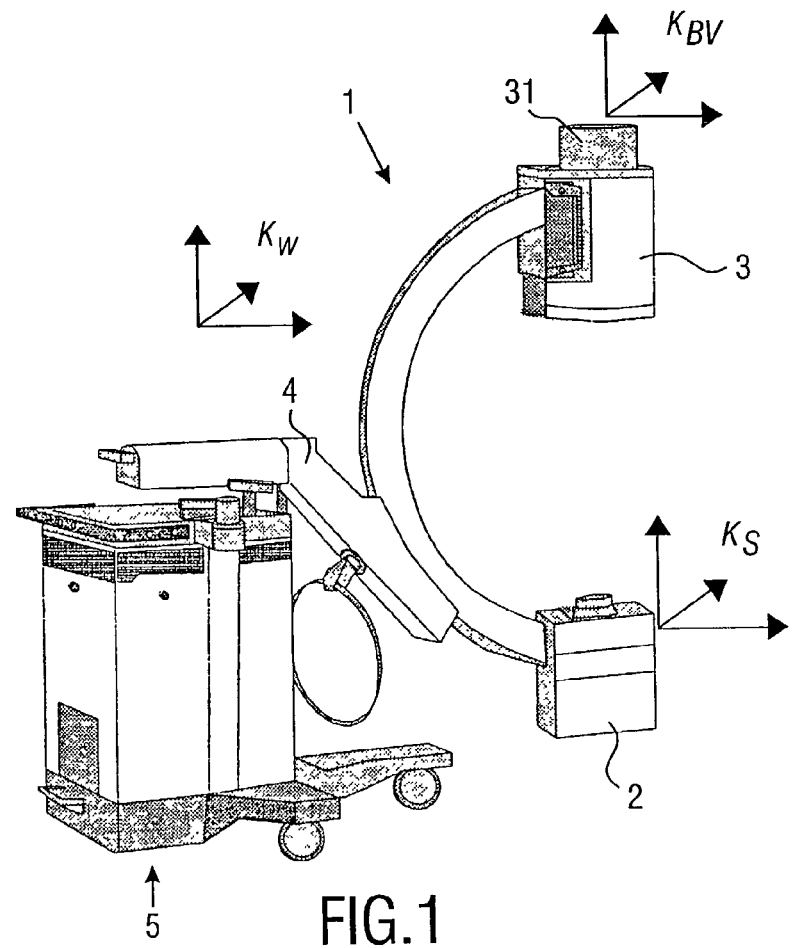
FIG. 1 is a diagrammatic overall view of an X-ray system provided with a device in accordance with the invention.

FIG. 1 shows a mobile X-ray system which includes a C-arm 1, at one end of which there is mounted an X-ray source 2 while an X-ray detector 3 with an image intensifier is mounted at the other end thereof. Moreover, a triaxial magnetometer 31 which measures the directions and the strength of the surrounding magnetic field is also mounted on the C-arm 1. The C-arm 1 is mounted so as to be pivotable on a mount 4 which itself is attached to a table 5. The table 5 is displaceable and provided with control elements and supply and operating devices for the X-ray system.

An object to be examined (a patient) is positioned between the source 2 and the detector 3; generally speaking, the C-arm 1 on the mount 4 can then be pivoted through an angle of at least 180° so as to enable optimum irradiation of the zone to be examined.

As has already been stated, notably the image intensifier can be disturbed by an external magnetic field or at least be influenced to such an extent that the acquired image is distorted. Therefore, a calibration is to be performed so as to compensate the magnetic field strengths which are dependent on the position of the image intensifier, thus correcting the different distortions caused thereby.

The calibration is performed after the manufacture of the X-ray system as well as possibly at regular intervals (service intervals). The essential steps of such a method will be described in detail hereinafter. However, modified versions of this method or other methods can alternatively be carried out.

Figure 2:
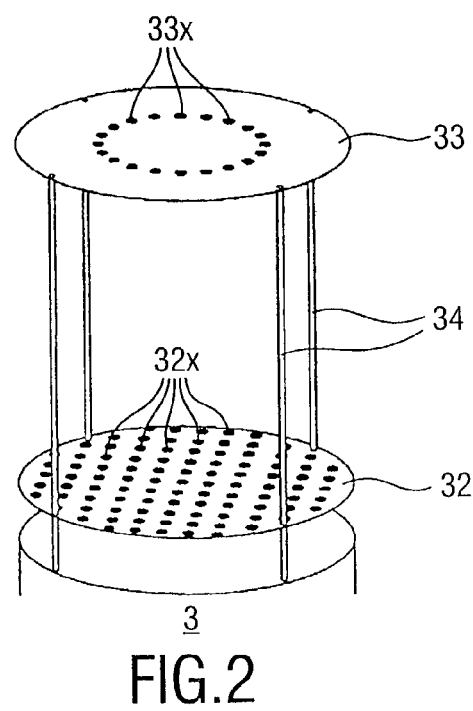
FIG. 2 is a diagrammatic representation of an arrangement for calibrating the X-ray system.

First a phantom object in the form of two parallel plates 32, 33 is attached to the X-ray detector 3 as shown in FIG. 2. Bars 34 which are also suitable for keeping the plates in parallel are provided for this purpose. The first plate 32 is situated directly in front of the entrance window of the detector 3 and is provided with a plurality of circular surfaces or spheres 32× which are arranged at grid points of an imaginary quadratic grid and are impervious to X-rays. Between the first plate 32 and the X-ray source 2 there is arranged the second plate 33 which is situated at a distance of, for example, approximately 37 cm from the first plate. The second plate is provided with a plurality of equally large and also X-ray impervious circular surfaces or spheres 33× which, however, are arranged along the circumference of a centered circle.

The first plate 32 serves to determine the distortion parameters of a projection image whereas the second plate 33 serves to determine the focal point position, that is, each time for a plurality of selected pivoted positions of the C-arm 1, that is, positions of the image intensifier as determined, for example, by means of a stationary camera. The distortion parameters and focal point positions determined are stored as distortion data sets for each position of the image intensifier.

More specifically, the circular surfaces or spheres 32× of the first plate 32 are projected onto the detector 3, are detected by means of a segmentation algorithm and associated with the individual circular surfaces or spheres 32× on the first plate whose positions are known. In conjunction with appropriate interpolation between the surfaces, the distortion parameters can thus be calculated in known manner for "each" X-ray beam and hence for each pixel.

Furthermore, the focal point position is calculated in known manner while using the image of the circle of circular surfaces 33× which is projected onto the detector by the second plate 33 and also while using the ratio of the diameter of this circle to that of the projected circle.

The distortion data sets acquired for each pivoted position of the C-arm 1, that is, for each position of the image intensifier, are then used to calculate calibration data (calibration base points) which is stored and is suitable for correcting the errors, caused by the distortions and focal point shifts, in an image acquired in the relevant position of the image intensifier.

Furthermore, in each of these positions of the image intensifier the triaxial magnetometer 31 measures the external magnetic field in the direct vicinity of the image intensifier, that is, in respect of its directions and its strength. This magnetic field data is then taken up, in association with the calibration data determined for this position, in a look-up table.

The calibration of the X-ray system is terminated when calibration data and magnetic field data has been determined and stored in the look-up table for an adequate number of pivoted positions of the C-arm 1 (that is, positions of the image intensifier).

For the sake of completeness it is to be noted that the determination of the calibration data can also be performed in a different manner, for example, by generating and external magnetic field in various positions instead of the movement of the image intensifier, said field being varied in respect of its directions and its strength in order to calculate the calibration data for the resultant distortions and to store this calibration data in the look-up table at the respective magnetic field data.

Alternatively, the look-up table could also be calculated on the basis of a physical model of the image pick-up device.

For the calibration, that is, for the formation and storage of the look-up table, either a separate arithmetic and storage unit is provided or the calibration is performed by means on an appropriate data processing program while utilizing an arithmetic unit already included in the relevant X-ray system.

For imaging during the examination of a patient or another object, the C-arm is first rotated as is customary, to a position in which the region of interest can be irradiated and a corresponding image can be projected onto the image intensifier. When this position is reached, the image is acquired in known manner. Furthermore, the triaxial magnetometer 31 measures the magnetic field surrounding the image intensifier in this position that is, in respect of its directions and its strength. This magnetic field data is then compared with the corresponding entries in the look-up table. When a corresponding or substantially corresponding entry is found, the calibration data associated with the relevant entry is read out and used for correcting the acquired image in known manner.

If no adequate correspondence is found between the magnetic field data determined and the magnetic field data stored in the table, the relevant calibration data must be interpolated. To this end, the calibration data is considered as calibration base points. Various methods can be used in this respect. The application of an approximated Delauney triangulation will now be described by way of example.

This is an approximation of the triangulation, because the calibration base points are situated on a spherical surface, but the Delauney triangles formed by the base points are to be treated as planar triangles for the sake of simplicity. Therefore, prior to the interpolation each base point must be projected onto such planar triangles.

The original (planar) method is executed as follows. Let there be a set of calibration base points to be interpolated on a spherical surface. The triangulation algorithm leads to a set of non-intersecting planar triangles whose corners are formed by respective calibration base points, so that the entire surface is covered by triangles.

Any intermediate point P (that is, a calibration base point to be interpolated) can then be unambiguously associated with one of the triangles. The corner points of this triangle constitute the three calibration base points which are nearest to the point P. The base points to be selected for the interpolation are thus determined.

The Delauney triangulation is unambiguous. For a two-dimensional plane the algorithm is as follows: first all feasible triangles are formed from the set of calibration base points. The triangles whose corner points are collinear are not taken into account. When the circle circumscribing a triangle contains other base points, the triangle is not taken into account either. The triangle is used only in the absence of these two events.

However, because the calibration base points are actually situated on a spherical surface, in order to avoid geometrical distortions and other problems the Delauney triangulation is adapted to a spherical interpolation and modified (approximated) in such a manner that the calibration base points are transformed in a three-dimensional cartesian co-ordinate system. For each triplet of coplanar base points the corresponding triangle is not taken into account.

Instead of the above circumscribed circle, an enclosing sphere is formed and the radius thereof is compared with the three-dimensional Euclidian distance from any other calibration base point. It can be demonstrated that this criterion is equivalent to the normal two-dimensional Delauney triangulation when the base points are situated on an ideal spherical surface. When the enclosing sphere contains other base points, the triangle is disregarded. The triangle can be used if this is not the case.

In order to simplify as well as to accelerate the interpolation calculations, the projection P' of the point P onto the plane triangle surface is considered instead of the point P on a spherical surface. This gives rise to minor distortion effects in the interpolation contributions, be it only in the case of large triangles.

When the triangulation is terminated, the interpolation by the planar triangles can be simply calculated while utilizing barycentric co-ordinates. A point P' situated in the plane (C1, C2, C3) can be described by its barycentric co-ordinates (B1, B2, B3). Hereinafter it is assumed that a point P on the spherical surface for which the interpolation coefficients are to be calculated is projected onto each planar triangle surface to be taken into account (point P').

The barycentric co-ordinates contain respective information concerning the relative position of the point P' in relation to one of the sides of the triangle. For a corner point C1 of the triangle the co-ordinate B1 is negative when the point P' lies beyond the line extending to the corner points C2 and C3; it is zero when it lies on this line and positive when it is situated at the same side of the line as the corner point C1.

The barycentric co-ordinates thus constitute a simple criterion for the localizing of the appropriate interpolation triangle. The point P' is situated within the triangle only if all values Bi are larger than 0.

After the determination of the barycentric co-ordinates, the values to be interpolated for the point P' can be determined by way of a simple linear combination, enabling the interpolated calibration base point to be calculated so as to correct the acquired image.

For the imaging and a possibly necessary interpolation there is provided either a separate arithmetic and storage unit or a corresponding data processing program which is executed by means of an arithmetic unit already present in the relevant X-ray system.

For the sake of completeness it is to be noted that the principle of the invention can be used not only for distortion correction of an acquired image, but also, for example, for surgical navigation. In that case it is not of prime importance to correct an acquired image for distortions; the aim is rather to determine as accurately as possible the position of an instrument (for example, a catheter) introduced into the patient and to reproduce this position in the acquired image by means of an appropriate image processing system.

On the one hand an X-ray image of the zone of a patient to be examined is then acquired in a conventional manner, without this image being corrected for distortion. On the other hand, the instantaneous position of the introduced instrument is continuously determined by means of a known method or a position measuring apparatus (for example, by means of a small transmitter or inductance provided at the tip of the instrument). This position is then distorted by (reverse) application of the look-up table describing the distortion properties of the X-ray apparatus. In other words, the (virtual) image of the introduced instrument is thus distorted in conformity with the imaging properties of the X-ray apparatus which are stored in the form of the calibration data. This distorted image is then reproduced, while using an appropriate display unit, in the acquired (distorted) X-ray image, so that the instrument appears in the X-ray image in the correct position.

This offers the advantage that only one X-ray image need be formed even in the case of continuous tracking or continuously updated reproduction of the (usually guided) instrument. Moreover, the instrument need not have been introduced yet when this image is formed, so that the X-ray image cannot be affected thereby either.

Distortion correction of the image is not necessary, because only the actual position of the instrument relative to the object to be examined is of importance.

What is claimed is:

1. A method for the calibration of an image pick-up device which is sensitive to magnetic fields, which method includes the following steps:
   determining calibration data in a plurality of positions of the image pick-up device, which calibration data is suitable for magnetic field induced distortion correction of an image acquired by the image pick-up device,
   measuring magnetic field data including magnetic field strength and direction which currently acting on the image pick-up device in a current position, and
   using the currently measured magnetic field data measured in the current position with the calibration data to correct the magnetic field induced distortion.

2. A method as claimed in claim 1, wherein determining calibration data further comprises acquiring calibration data by means of a phantom object.

3. A method as claimed in claim 1, wherein determining calibration data further comprises calculating calibration data by means of a physical model of the image pick-up device.

4. A method for imaging by means of an image pick-up device calibrated for distortion correction of an image of an object to be examined, which method includes:
   acquiring an image of the object to be examined,
   measuring magnetic field data descriptive of a magnetic field which is currently acting on the image pick-up device causing distortions to the image,
   comparing the measured magnetic field data with magnetic field data previously stored in a look-up table,
   comparing the determined magnetic field data with magnetic field data previously stored in a look-up table,
   reading out calibration data associated with the stored magnetic field data which corresponds at least essentially to the determined magnetic field data,
   determining the position and acquiring an image of an instrument introduced into the object to be examined,
   calculating a corrected image of the image with the instrument introduced into the object, by at least means of the calibration data read out, and
   reproducing the corrected image of the introduced instrument in the acquired image of the object to be examined.

5. The method of claim 4, wherein the method is performed by a data processing program executed in a computer.

6. The method as set forth in claim 4, further including:
   determining a correspondence between the measured magnetic field data and the previously stored magnetic field data;
   if there is no substantial correspondence is determined, interpolating the calibration data which includes:
   connecting calibration base points with one another to form a plurality of non-intersecting triangles, the triangles lying on a spherical surface,
   transforming the triangles into a 3D Cartesian coordinate system,
   projecting non-correspondent magnetic field data points into the transformed triangles, and
   calculating the interpolated calibration data for the non-correspondent magnetic field points by an approximated triangulation.

7. An apparatus including:
   a look-up table for storing calibration data for correcting magnetic field induced distortions in images from an image pick-up device distorted by each of a plurality of preselected magnetic fields, the look-up table correlating calibration data with preselected magnetic fields data descriptive of the plurality of preselected magnetic fields;
   a triaxial magnetometer for determining current magnetic field data descriptive of magnetic fields currently acting on the image pick-up device;
   an arithmetic and storage unit for comparing the current magnetic field data with the preselected magnetic fields data of the look-up table, for reading out stored calibration data which corresponds at least essentially to the current magnetic field data for removing distortions from a currently acquired image; and
   a display unit for displaying the distortion-corrected image.

8. The X-ray system claimed in claim 7, wherein the image pick-up device includes an image intensifier.

9. A method for imaging surgical navigation, by means of an image pick-up device which is calibrated for distortion correction of an image of an object to be examined, which method includes:
   acquiring an image of an object to be examined,
   determining magnetic field data which acted on the image pick-up device during the acquiring of the image,
   reading out calibration data associated with the previously stored magnetic field data which corresponds at least essentially to the measured magnetic field data, and
   removing the magnetic field distortions from the acquired image by means of the calibration data read out.

10. The method of claim 9, wherein the method is performed by a data processing program executed in a computer.

* * * * *